United States Patent [19]
Engelhardt et al.

[11] Patent Number: 5,496,306
[45] Date of Patent: Mar. 5, 1996

[54] PULSE STRETCHED SOLID-STATE LASER LITHOTRIPTER

[75] Inventors: Ralf Engelhardt, Uetze; Ralf Brinkmann, Nordstemmen, both of Germany; John C. Walling, Whitehouse Station; Donald F. Heller, Boundbook, both of N.J.

[73] Assignee: Light Age, Inc., Somerset, N.J.

[21] Appl. No.: 982,022

[22] Filed: Nov. 24, 1992

Related U.S. Application Data

[63] Continuation of Ser. No. 585,992, Sep. 21, 1990, abandoned.

[51] Int. Cl.$^6$ .................................................. A61B 17/22
[52] U.S. Cl. ............................. 606/15; 606/2.5; 606/3; 601/2
[58] Field of Search ..................... 606/15, 2, 7, 127, 606/128, 2.5, 3; 601/2, 4

[56] References Cited

U.S. PATENT DOCUMENTS

| | | | |
|---|---|---|---|
| 4,791,927 | 12/1988 | Menger | 606/3 |
| 4,887,600 | 12/1989 | Watson et al. | 606/128 |
| 4,968,314 | 11/1990 | Michaels | 606/7 |
| 4,994,059 | 2/1991 | Kosa et al. | 606/9 |
| 5,009,658 | 4/1991 | Damgaard-Iversen et al. | 606/128 |
| 5,041,121 | 8/1991 | Wondrazek et al. | 606/15 |
| 5,059,200 | 10/1991 | Tulip | 606/128 |
| 5,196,004 | 3/1993 | Sinofsky | 606/15 |
| 5,342,198 | 8/1994 | Vassiliadis et al. | 606/15 |

FOREIGN PATENT DOCUMENTS

| | | | |
|---|---|---|---|
| 3711086 | 10/1988 | Germany | 606/2.5 |
| 9009762 | 9/1990 | WIPO | 128/DIG. 28 |

OTHER PUBLICATIONS

Brinkmann et al., Laser Induced Shockwave Lithotripsy by use of an 1 µs Alexandrite Laser, SPIE vol. 1200, at least Jun. 1990, pp. 67–74.
Fair, Medical Instrumentation, vol. 12, No. 2, Mar.–Apr. 1978, pp. 100–104.
Bhatta, "Acoustic and Plasma Guided Lithotripsy of Urinary Calculi", vol. 142, Aug., 1989, Journal of Urology.
Watson, "A Survey of the Action of Lasers on Stones", Laser Lithotripsy, ed Steiner (R), Springer–Verlag, Germany, 1988 pp. 14–23.
Kuper, "Medical Applications of Alexantrite Laser Systems", pp. 183–184, 1987.

Primary Examiner—William E. Kamm
Assistant Examiner—Brian L. Casler
Attorney, Agent, or Firm—Morgan & Finnegan

[57] ABSTRACT

A method of laser lithotripsy is disclosed that utilizes pulse stretched Q-switched solid state lasers in conjunction with relatively small diameter optical fibers to achieve effective breakup of calculi located within the body, such as kidney and gall stones.

9 Claims, 2 Drawing Sheets

PULSE STRETCHED SOLID-STATE LASER LITHOTRIPTER

This is a continuation of application Ser. No. 07/585,992, filed on 21, Sep. 1990, now abandoned.

BACKGROUND OF THE INVENTION

This invention relates to a method of laser lithotripsy and more particularly to a method of laser lithotripsy using stretched Q-switched pulse solid-state lasers.

The treatment of renal lithiasis has advanced dramatically (C. G. Chaussy, G. J. Fuchs, "Extracorporeal Shockwave Lithotripsy", *Monogr. Urol.* 8:80 (1987); J. W. Segura et al., "Percutaneous Lithotripsy", *J. Urol.* 30:1051 (1983); J. W. Segura, D. H. Bagley, H. W. Schoenberg et al., "Transurethral Removal of Large Ureteral and Renal Pelvic Calculi Using Urethroscopic Ultrasonic Lithotripsy", J. Urol. 130:31 (1983) since a decade ago when Fair outlined the basic concept (H. D. Fair, "In Vitro Destruction of Urinary Calculi by Laser-Induced Stress Waves", *Medical Instrumentation* 12(2):100 (1978)). The development of percutaneous access to the kidney and "endorologic" destruction of kidney stones was followed closely by the development of extracorporeal shock wave lithotripsy (ESWL). The combination of these techniques has markedly decreased the need for open surgical removal of renal stones and ureteral stones. There are currently a number of techniques for treating stones within the ureter including ureteral cathertization, stone basketing, and ultrasonic lithotripsy (C. Chaussy, G. Fuchs, R. Kahn et al., "Transurethral Ultrasonic Ureterolithotripsy Using a Solid Wire Probe", *Urology* 29:531 (1987). The latter, although effective requires dilation of the distal ureter for access to the stone. Ureteral dilation can be traumatic and may lead to ureteral injury.

The most promising new technology for ureteral stone fragmentation is laser lithotripsy using a pulsed laser (G. M. Watson and J. E. A. Wickham, "Initial Experience with a Pulsed Dye Laser for Ureteric Calculi", *Lancet* 1357 (1986). Optical fiber delivery systems for pulsed lasers having diameters as small as 200 microns can transmit enough energy to fragment stones. The concomitant development of very small uretheroscopes now permits atraumatic urethroscopy in combination with the pulsed laser stone fragmentation.

The pulsed dye laser, which emits pulses of approximately 1 µs in duration, have been used successfully in clinical lithotripsy procedures. Dye lasers are,, however, less favorable than solid state lasers from the standpoint of size, reliability, ease of use, and ease of maintenance. Despite the general preference of solid state lasers over dye lasers from this standpoint, comparatively little success has been obtained with them in the lithotripsy application. Studies have shown that these lasers typically emit pulses either too short not to destroy the critical optical fiber or too long to be effective in breaking up the calculi.

Techniques have been developed in order to limit damage to tissues of the urinal tract by the laser beam. In one such technique developed for and used in dye laser lithotripters, the back scattered light, which is generated in the targeted material and passes back through the optical fiber, is used to preempt the continued development of the laser pulses before a plasma can be created in the event that the targeted material is not that of calculi. This so called "stone recognition system" has proved very effective in reducing damage to normal tissue.

SUMMARY OF THE INVENTION

It is the object of the present invention to provide an improved method of laser, such as a LiCAF laser lithotripsy using stretched Q-switched pulse solid-state lasers and most especially stretched Q-switched pulse Alexandrite lasers (J. C. Walling, "Tunable Paramagnetic-Ion Solid-State Lasers", *Topics in Applied Physics,* 59, Chap. 9, Ed. L. F. Mollenhauer, Springer-Verlag, New York; R. Brinkmann, W. Meyer, R. Engelhardt, J. C. Walling, "Laser Induced Shockwave Lithotripsy by Use of an 1 µm Alexandrite Laser"). The stretched pulsed Alexandrite laser is capable of emitting pulses with durations of approximately 1 µs needed for successful passage through the optical fiber and effective calculi fragmentation. Non-stretched pulsed Alexandrite lasers typically emit pulses in the range of 30 to 300 ns. The Alexandrite laser emits directly in the therapeutic window (wavelengths between about 700 nm and 1 nm) and produces minimal damage to tissue. Alexandrite lasers have characteristically slower pulse buildup time and it is consequently easier to control the pulse duration then in Nd:YAG and several other candidate lasers.

Pulse stretching can be achieved by, but is not limited to, fast electrooptics feedback techniques by which the laser emission is detected and the resulting signal used to control or limit the optical power in laser resonator during Q-switched operation. As a result, the energy stored in the laser rod and released by the activated Q-switch takes longer to exit the resonator then passive resonator kinetics would dictate. This process produces laser pulses of longer pulse duration.

The disclosed method employs such a stretched pulse solid state laser Coupled to a 200 to 800 µm optical fiber, either with or without a stone recognition system to identify the presence of the calculi in the beam and terminate the pulse prematurely in the event it is not detected. The distal termination of the optical fiber may be by a lens, but typically the termination is bare and need not be specially prepared. A broken fiber end is suitable. A pulse duration in the range of 0.5 to 3 µs or preferably 0.8 to 1.5 µs and a pulse energy of between about 15 and 200 mJ, preferably between about 30 and 100 mJ can be used in the present method.

BRIEF DESCRIPTION OF THE DRAWINGS

The accompanying drawings, which are incorporated in and form a part of the specification, illustrate the present invention and, together with the description, serve to explain the principles of the invention. In the drawings.

DETAILED DESCRIPTION OF THE INVENTION

In the following the present invention is described by way of experiments performed according thereto and the results obtained thereby.

Pulse Stretching

Figure 1:
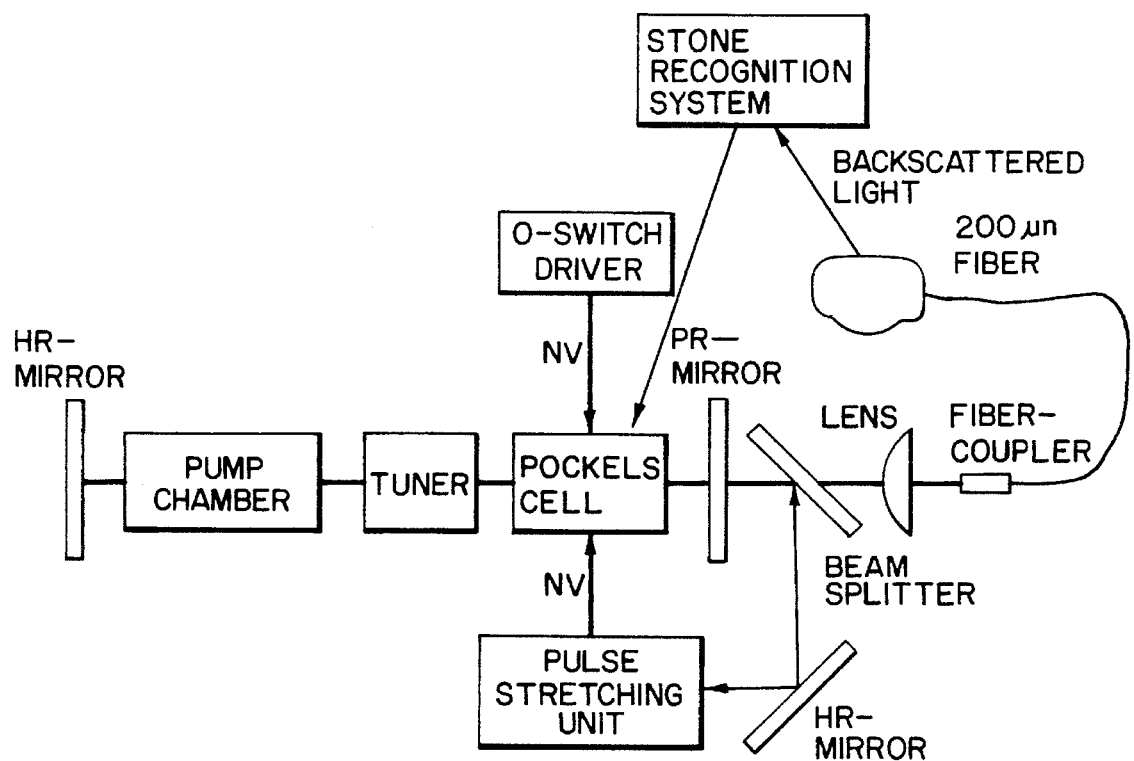
FIG. 1 is schematic block diagram showing an experimental setup of a pulse stretched alexandrite laser lithotripter.

FIG. 1 illustrates schematically the method by which the Alexandrite laser pulse was stretched to the 1 µs range: The HR-mirror (on left), pump chamber, tuner, pokels cell, Q-switch driver, PR-Mirror are all part of the Alexandrite laser oscillator which in the case of the experiments described herein was a Model LAI-101PAL pulsed Alexandrite laser manufactured by Light Age, Inc. Warren, N.J. The beam splitter, HR-mirror (right) and pulse stretching unit are components added to provide the feedback to the laser oscillator in order to stretch the pulse. The lens, fiber coupler and 200 μm fiber are components of the beam delivery system and are well understood standard equipment, conventionally used for laser lithotripsy.

Without the active feedback circuit the Q-switch pulse width is determined by the cavity lifetime and the extent above threshold is the inversion at which the Q-switch is activated. With active feedback, the energy stored in the laser rod is emitted over a longer time because the intracavity power density is limited by the active feedback. It is this intracavity power density that determines the rate of energy extraction from the excited laser rod (gain medium). By limiting the intracavity power density the stored energy in the rod takes a longer time to extract. The maximum pulse duration is limited by the fluorescence storage time of the laser rod itself.

The emission cross-section in Alexandrite, which determines the rate at which a given flux will extract the stored energy, is approximately $10^{-20}$ $cm^{-1}$, which is about 1/30th that of Nd:YAG. This comparatively low cross-section is the reason why the kinetics in Alexandrite are slow and the pulse duration more easily controlled by available technology.

The particular pulse stretching unit used in these experiments incorporates a high speed, high voltage vacuum photodiode, to achieve the required function. There are several established alternative high speed, high voltage amplifiers that can be used. Speed and voltage are relatively difficult to achieve simultaneously in one device. The options available may be increased by reducing the voltage requirement through the expedient of using more than one pockels cell in the resonator. The multiple pockels cells are in series optically, but are driven in parallel.

For these experiments, two KDT*P pockels cells were used and the crystals surfaces were at Brewster's angle as were the windows on the pockels cell. More standard pockels cells with perpendicular antireflection coated surfaces are also suitable.

Fiberoptic Delivery

For the clinical use of quartz fibers transmitting the required laser energy, the consumption of the fiber tip due to breakage must be very small to avoid adverse effects to the patient. The 2 μs long laser pulses of the pulsed dye laser do not cause high fiber consumption. For determination of this problem for Alexandrite lasers, a 200 μm quartz fiber after 250 shots fiber was held adjacent to a "standard" aluminum surface that simulates the stone. The pulse energy was 40 mJ. The pulse shape was rectangular. Pulse lengths longer than 600 ns (power density smaller than about 200 $MW/cm^2$) led to a fiber consumption of about 0.3 mm/100 shots which rises dramatically by two orders in magnitude to about 30 mm/100 shots if the pulse length is smaller than about 500 ns.

Stone Fragmentation

The dynamics of stone breakage depends on the kinetic reaction to the discharge of a plume of stone material. Generally, the plume is produced by the creation of incandescent gases from the surface material of the stone. These gases are not necessarily a true plasma, but nevertheless have much stronger absorption properties than does the stone itself. Thus, once the plume of incandescent gas is produced it continues to absorb the remaining energy from the laser pulse. It also expands and cools, having an effective life of about 1 μs. This time is also the time that the shock wave created by the plasma travels across the stone. The period of 1 μs is consequently close to the optimum pulse duration, with some minor variation for geometry and the particular material of the stone.

The principal problem is the creation of the plume (plasma). Once the pulse energy and pulse duration is sufficient to create the plume, the stone breakage follows in due course. Certain types of stones, those light in color, are particularly difficult to break primarily because it is difficult to initiate the plume formation. It is possible to enhance the plume initiation for such stones by use of a small amount of second harmonic from the Alexandrite laser mixed in with the fundamental. This is achieved by introducing a second harmonic crystal such as KDP or BBO in the beam prior to its entering the fiber.

Figure 2:
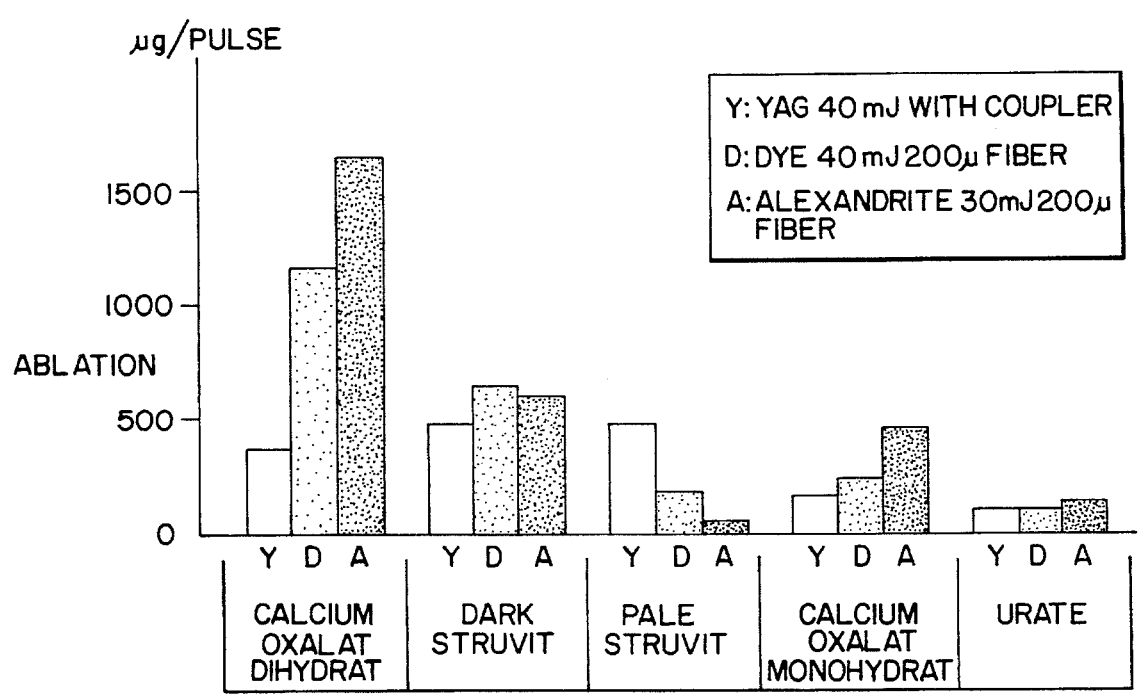
FIG. 2 is a graph showing the fragmentation rates for different laser lithotripsy systems.

The stones evaluated included (1) calcium oxalate dihydrate; (2) dark struvite; (3) pale struvite; (4) calcium oxalate monohydrate; and (5) urate. The fragmentation rates for different laser lithotripsy systems is shown in FIG. 2. The threshold for plasma ignition depends mainly on the power density and energy density. If the power density exceeds a threshold of about $10^8 W/cm^2$ between 30 and 60 $J/cm^2$ is needed to generate a plasma for dark stones (having high absorption coefficient). Calculi of lower absorption coefficient, for example struvit stones, require higher pulse energies to form plasma.

What is claimed is:

1. An apparatus for conducting laser lithotripsy comprising a pulse-stretched solid state laser having a wavelength between 700 nm and 1.0 μm and a fiber optic delivery means for conducting laser light, said pulsed solid state laser having a feedback means for controlling pulse duration wherein the pulse duration is in the range of 0.5 to 3 μs, and said pulse energy being between 15 and 200 mJ.

2. The apparatus of claim 1, wherein the solid state laser is an Alexandrite laser.

3. The apparatus of claim 1, wherein the solid state laser is a tunable laser.

4. The apparatus of claim 1, wherein the solid state laser is a LiCAF laser.

5. A method of laser lithotripsy for breaking calculi within the body, said method comprising providing a pulse-stretched solid state laser having a wavelength between 700 nm and 1.0 μm with a pulse duration in the range of 0.5 to 3 μs and a fiber optic delivery means for conducting laser light to the calculus, emitting the laser light from the laser, conducting the laser light through the delivery means to the calculus and breaking the calculus.

6. The method of claim 1, wherein the pulse duration is in the range from 0.8 to 1.5 μs.

7. The method of claim 1, wherein the pulse energy is between 30 and 100 mJ.

8. The method of claim 5, comprising using an admixture of the second harmonic of the fundamental to assist in plasma initiation.

9. The method of claim 1, wherein the laser has a pulse energy between 15 and 200 mJ.

* * * * *